United States Patent [19]

Sampathkumar

[11] Patent Number: 4,594,437

[45] Date of Patent: Jun. 10, 1986

[54] PROCESS FOR RECOVERING TOCOPHEROLS FROM DEODORIZER SLUDGE

[75] Inventor: Sampathkumar, Lincroft, N.J.

[73] Assignee: UC Unitas Corporation, New York, N.Y.

[21] Appl. No.: 703,694

[22] Filed: Feb. 21, 1985

[51] Int. Cl.⁴ .............................................. C07D 311/72
[52] U.S. Cl. ...................................................... 549/413
[58] Field of Search ......................................... 549/413

[56] References Cited

U.S. PATENT DOCUMENTS 2,349,270  5/1944  Hickman ............................. 549/413
3,153,054 10/1964  Brown ................................. 549/413
3,335,154  8/1967  Smith .................................. 549/413

*Primary Examiner*—Nicky Chan
*Attorney, Agent, or Firm*—Brumbaugh, Graves, Donohue & Raymond

[57] ABSTRACT

Tocopherols are recovered from deodorizer sludge by urea complex formation with the contaminating fatty acids and glycerides of fatty acids in the presence of a solvent.

14 Claims, No Drawings

PROCESS FOR RECOVERING TOCOPHEROLS FROM DEODORIZER SLUDGE

BACKGROUND OF THE INVENTION

The present invention relates to the recovery or purification of tocopherols (Vitamin E) and in particular it relates to a process wherein loss of activity or yield during recovery or purification is completely eliminated.

Deodorizer sludge or distillate obtained from natural fats and oils is a complex mixture of tocopherols, sterols, fatty acids, fatty acid glycerides, hydrocarbons, waxes, pigments, water and other materials. The concentration of tocopherols in the deodorizer sludge usually varies from 1% to 15% by weight.

There are several processes for recovering or purifying tocopherols from low-concentration tocopherol materials. These processes involve splitting of the complex glycerides by acid catalyzed hydrolysis, esterification, saponification, solvent fractionation, molecular distillation, ion-exchange adsorption and so forth. These processes involve drastic treatment to heat, oxidizing agents, action of mineral acid or alkali.

SUMMARY OF THE INVENTION

The principal object of the present invention is to provide an efficient, economical and chemically mild process for recovering tocopherols from deodorizer sludge for use in pharmaceutical and food applications without loss of vitamin E activity.

This object is achieved by the present invention which is based on the discovery that urea forms an inclusion complex with $C_6$ to $C_{22}$ fatty acids and fatty acid glycerides, in which hydrogen-bonded urea molecules are oriented in a helical lattice into which the fatty acid or the fatty acid glyceride molecule fits.

According to the present invnetion, it has been found unexpectedly that urea forms the inclusion complex with all the fatty acids and glycerides of fatty acids without entrapping the sterols, tocopherols and other bulky molecules present in the deodorizer sludge or distillate.

Accordingly, the present invention provides a process for recovering tocopherols from deodorizer sludge containing tocopherols, fatty acids and glycerides of fatty acids which comprises:

forming a mixture of the deodorizer sludge and a solution of urea dissolved in a solvent for urea, heating the mixture to form a urea complex of the fatty acids and glycerides of fatty acids, cooling the mixture to precipitate the urea complex from a mother liquor containing the tocopherols, and separating the mother liquor from the precipitate.

The process can further comprise concentrating the mother liquor, and separating residual solids from the mother liquor. The process can still further comprise extracting the mother liquor to form an oil rich in tocopherols.

Thus, the process of the present invention makes possible the production of a high potency tocopherol concentrate by reacting urea with the deodorizer sludge comprising tocopherols, sterols, fatty acids, glycerides of fatty acids, hydrocarbons, waxes, pigments, water, etc., in the presence of a suitable solvent like aliphatic alcohols with 1 to 5 carbon atoms, such as methanol, ethanol, butanol, isopropyl alcohol; or ketones, such as methyl ethyl ketone, 2-pentanone; or aromatic hydrocarbons, such as benzene, toluene, xylene; or branched aliphatic hydrocarbons, such as isooctane, isopentane. In general, lower monohydric alcohols which are miscible with water, which have great hydrogen bonding capacity, and also dissolve urea under hot or cold conditions without decomposing or damaging the product formed tend to be suitable solvents. Methanol and ethanol are preferred solvents.

The molar ratio of urea to total fatty acids and glycerides of fatty acids is from about 5:1 to 25:1; a preferred molar ratio is 13.5:1 to 14.5:1. The molar ratio of urea to solvent for urea is generally from about 1:1 to 1:75; a preferred molar ratio is 1:1 to 1:40.

A temperature range of about 40° C.–78° C. is generally useful for the urea complex formation. However, for deodorizer sludge containing long chain fatty acids, such as stearic, oleic, linoleic and linolenic acid, it is found to be about 40° C.–65° C.

The heating time of reaction is from about 15 minutes to about 90 minutes; a preferred heating time is 60 minutes.

The urea complex formation and work-up depend on the pH of the reaction medium. The preferred pH range is about 6.0–10.5. Although a slightly lower (acidic) or higher (alkaline) pH range does not affect the urea complex formation, it will damage the sensitive tocophenol molecules.

DETAILED DESCRIPTION OF THE INVENTION

Fatty acids and the glycerides of fatty acids varying in chain length from $C_6$ to $C_{22}$ are separated in the present process by reaction with urea to form a urea complex in the presence of sterols, tocopherols, hydrocarbons, waxes, pigments, water and other materials. The property of urea to form adducts with these types of compounds has not been utilized for the purification of biologically active compounds, especially tocopherols. The complex formation has been conducted previously with purer materials and has not been explored on an industrial scale.

The present invention is used to form the complex of urea with fatty acids and fatty acid glycerides in spite of the complex nature of the starting materials. Only those compounds having long chain methylene bridges are expected to work satisfactorily.

If more than 15% of oleic acid is present in the deodorizer sludge, the preferred molar ratio of urea to oleic acid is 14:1; methanol is the preferred solvent; and the boiling point of methanol (64° C.–65° C.) is the preferred temperature range.

If more than 15% palmitic acid or glycerides of palmitic acid are present in the deodorizer sludge, the preferred molar ratio of urea to palmitic acid or glycerides of palmitic acid is 8:1.

The instability of the urea complex of fatty acids can be utilized for further purification of fatty acids and their separation. The urea complex can be broken down to urea and the respective fatty acid in the presence of water at a temperature of 60° C.–85° C. and in the presence of a catalytic amount of a mineral acid. Sulfuric acid (50%) is generally used.

The preparation of an inclusion complex of urea with fatty acids or their glycerides or fatty acid esters in the presence of several types of compounds like tocopherols, sterols, hydrocarbons, waxes, pigments, water, etc., generally starts by dissolving urea in a solvent therefor, particularly methanol containing 2.5% to 5.0% water. The reaction temperature is controlled so as not to go above about 64° C. in the case of methanol as the solvent and about 78° C. when ethanol is used as the solvent. The contents are kept at this temperature for about 60–90 minutes and cooled to about 0° C.–5° C. for about 6 to 8 hours. The solids filtered off and the filtrate rich in tocopherols, sterols, waxes, pigments, etc., are used for further purification.

The mother liquor can be extracted or stripped with an appropriate extractant, such as chloroform, hexane or methylene chloride.

The following examples further illustrate the process of the present invention. The reported assays for tocopherols, sterols, fatty acids and glycerides were done by GLC (gas liquid chromatography) or TLC (thin layer chromatography) analysis.

EXAMPLE 1

This example illustrates the treatment of deodorizer sludge with urea to recover tocopherols, wherein the molar ratios of fatty acids and glycerides to urea to methanol are 1:10:90.

1000 grams of the deodorizer sludge assayed at 85% fatty acids and glycerides, 6% tocopherols, 3% sterols and the remainder being unidentified material were added into a reactor vessel (equipped with a mixer) containing a solution of 1758 grams (29 moles) of urea dissolved in 8400 grams (262 moles) of methanol. The temperature of the mixture was slowly raised to 64° C. and the mixture was refluxed at 64° C. for 60 minutes. The refluxed mixture was cooled gradually to 0° C. (about 6 hours), whereupon a precipitate formed in the mixture. The precipitated solids were filtered off and the mother liquor or filtrate rich in tocopherols was concentrated to ⅓ its volume. The pH of the concentrated filtrate (about 8.5) was adjusted to a value of 5.8 by adding citric acid (10%). The residual solids were again filtered off and the mother liquor or filtrate concentrated to an oil. Some more solids appeared and the entire oil was extracted with 500 milliliters of chloroform. The chloroform extract after concentration yielded a red oil free of solids.

The oil assayed at 42% tocopherols, mainly $\beta$, $\gamma$ and $\delta$ with less than 5% of $\alpha$-tocopherol. The yield of tocopherols in the oil was 75%.

EXAMPLE 2

This example illustrates the treatment of deodorizer sludge with urea to recover tocopherols, wherein the molar ratios of fatty acids and glycerides to urea to methanol are 1:10:38.

250 grams of the deodorizer sludge assayed at 80% fatty acids and glycerides, 8% tocopherols, 7% sterols and the remainder being unidentified material were slowly added into the reactor vessel containing a clear solution of 675 grams (11 moles) of urea dissolved in 1.7 liters (42 moles) of hot methanol (60° C.). The mixture was refluxed at 64° C. for 45 minutes and then cooled to 0° C., whereupon a precipitate formed in the mixture. The precipitated solids were filtered off and the mother liquor or filtrate rich in tocopherols was concentrated to ½ its volume and cooled again (0° C.). A second crop of crystals which appeared were filtered off and the mother liquor or filtrate extracted with hexane (1:1 by volume). The hexane extract was concentrated to yield a red oil free of solids.

GLC analysis of the oil assayed at 38% tocopherols and the yield of tocopherols was 85%.

EXAMPLE 3

This example illustrates the treatment of deodorizer sludge with urea to recover tocopherols, wherein the molar ratios of fatty acids and glycerides to urea to methanol are 1:10:43.

500 grams of the deodorizer sludge assayed at 75% fatty acids and glycerides, 13% tocopherols, 3% sterols and the remainder being unidentified material were used for the urea complex formation. 1231 millimeters (30 moles) of methanol were charged into the reactor vessel and 480 grams (8 moles) of urea were added. The mixture was heated (64° C.) to get a clear solution. The deodorizer sludge (500 grams) was added to the hot urea solution and mixture refluxed (64° C.) for 30–35 minutes.

At this stage, another 324 grams (5 moles) of urea dissolved in 1068 milliliters (26 moles) of methanol (45°–50° C.) were added into the reactor vessel and refluxing at 64° C. continued for another 35 minutes. The reaction was discontinued and the mixture was cooled gradually to 0° C. The precipitated urea complex was filtered off and the filtrate concentrated to ½ its volume and extracted with methylene chloride (1:1 by volume).

The methylene chloride layer on GLC analysis assayed at 50% tocopherols and 9% sterols.

EXAMPLE 4

This example illustrates the use of ethyl alcohol (ethanol) as the solvent in the urea complex reaction. In this experiment the molar ratios of fatty acids and glycerides to urea to ethyl alcohol are 1:10:40.

250 grams of the deodorizer sludge assayed at 80% fatty acids and glycerides, 8% tocopherols, 7% sterols and the remainder being unidentified material were added into the reactor vessel containing a total of 432 grams (7 moles) of urea dissolved in 1656 milliliters (28 moles) of 95% ethyl alcohol at a temperature of 70° C. Urea was added in two portions as in Example 3. After refluxing (78° C.) for 60 minutes, the reaction was discontinued. The reactants were cooled to 0° C., the solids filtered off and the filtrate concentrated.

GLC analysis of the oil assayed at 24% tocopherols.

EXAMPLE 5

This example illustrates that longer refluxing time does not improve the concentration of tocopherols. In this experiment the molar ratios of fatty acids and glycerides to urea to methanol are 1:15:50.

The reactor vessel was charged with 907.2 grams (28 moles) of methanol and 283.5 grams (5 moles) of urea. The mixture was heated until a clear solution was obtained. 250 grams of a deodorizer sludge containing 70% fatty acids and glycerides were added over a period of 10 minutes. It was refluxed (64° C.) for 75 minutes.

Another 283.5 grams (5 moles) of urea and 200 milliliters (5 moles) of methanol were added at this stage and refluxing (64° C.) continued for another 30 minutes. The reaction was terminated by cooling to 0° C. and the solids were filtered off. The wet cake was washed (2×500 milliliters) with methylene chloride and the washings combined.

The methanol filtrate after freeing from solids and concentrating analyzed by GLC at 29% tocopherols.

The methylene chloride fraction from the wet cake analyzed at 12.9% tocopherols.

EXAMPLE 6

This example illustrates the increase in yield and concentration of tocopherols when excess methanol is used in the urea complex reaction. The molar ratios of fatty acids and glycerides to urea to methanol are 1:15:55.

360 grams (11 moles) of methanol were charged into the reactor vessel and 180 grams (3 moles) of urea were added and the mixture was refluxed (64° C.) to get a clear solution. 150 grams of the deodorizer sludge were added and the mixture was refluxed (64° C.) for 30 minutes.

Another 180 grams (3 moles) of urea in 344 grams (11 moles) of hot methanol were added into the reactor vessel and reflux was continued at 64° C. for another 30 minutes. The product was worked up as in Example 5.

The resulting red oil from the methanol filtrate analyzed by GLC at 32% tocopherols and the methylene chloride washings of the wet cake analyzed at 13% tocopherols for an overall yield of 97%.

EXAMPLE 7

This example illustrates the improvement in the tocopherol concentration wherein urea complex formation is done successively. The first urea complex formation was done at molar ratios of fatty acids and glycerides to urea to methanol of 1:10:90.

The reactor vessel containing a hot solution (58° C.) of 1758 grams (29 moles) of urea dissolved in 8400 grams (262 moles) of methanol was charged with 1000 grams of deodorizer sludge (assayed at 85% fatty acids and glycerides and 8.4% tocopherols). The reactants were refluxed (64° C.) for 60 minutes and cooled to 0° C. over several hours. The solids were filtered off and the methanol filtrate concentrated to ½ its volume. By GLC analysis, the concentrate assayed at 37% tocopherols.

This concentrate was again complexed with urea at molar ratios of fatty acids and glycerides to urea to methanol of 1:10:40 and the experiment conducted as before. The methanol filtrate after work-up analyzed at 55% tocopherols and a yield of 97%.

The following three examples using urea-type compounds as prospective complexing agents are for comparison with the process of the present invention using urea as the complexing agent.

EXAMPLE 8

This comparative example demonstrates that urea cannot be satisfactorily replaced by thiourea which also has a strong hydrogen bonding capacity, solubility in methanol and possesses a larger sulfur atom. The molar ratios of fatty acids and glycerides to thiourea to methanol used are 1:10:42.

The reactor vessel was charged with 380 grams (5 moles) of thiourea and 665.6 grams (21 moles) of methanol. The mixture was heated with stirring until an almost clear solution was obtained. 250 grams of deodorizer sludge assayed at 58% fatty acids and glycerides and 3.5% tocopherols were added into the reactor vessel and the mixture stirred at reflux temperature (64° C.) for 60 minutes.

At this stage, 60 grams (1 mole) of urea dissolved in 100 grams (3 moles) of hot methanol were added and the mixture refluxed (64° C.) for 15 minutes. The dark brown solution was cooled in the refrigerator, solids filtered off and the filtrate concentrated.

The concentrate by GLC analysis assayed at only 10.7% tocopherols and about 40% fatty acids.

EXAMPLE 9

This comparative example was conducted using 1,3-diethyl thiourea as the complexing agent, which did not effectively complex the fatty acids and glycerides in the deodorizer sludge. The molar ratios of fatty acids and glycerides to 1,3-diethyl thiourea to methanol are 1:10:48.

In the reactor vessel containing 191.4 grams (1.45 moles) of 1,3-diethyl thiourea dissolved in 228.5 grams (7 moles) of methanol, there were added 50 grams of deodorizer sludge assayed at 80% fatty acids and glycerides. The reaction mixture was refluxed (64° C.) with stirring for 45 minutes. The reaction was then terminated by cooling to ambient temperature.

Although some complex was formed, the tocopherol concentration in the mother liquor did not improve.

EXAMPLE 10

This comparative example demonstrates that increase in the nitrogen atoms of urea as in the case of dicyandiamide does not increase the concentration of tocopherols.

In the reactor vessel containing 126 grams (1.5 moles) of dicyandiamide dissolved in 1000 milliliters (25 moles) of hot methanol, there were added 100 grams of deodorizer sludge assayed at 7.5% tocopherols. The contents were refluxed (64° C.) for 60 minutes and cooled. The solids were filtered off (contained mostly unreacted dicyandiamide) and the filtrate concentrated to about 33 grams. It assayed by GLC at 11% tocopherols.

As is well known to those skilled in the tocopherol or Vitamin E art, deodorizer sludge as used in the process of the present invention is a waste product from steam refining or air blowing vegetable or cereal grain oils, such as soybean oil, cottonseed oil, wheat germ oil, corn oil, peanut oil and the like.

What is claimed is:

1. A process for recovering tocopherols from deodorizer sludge containing tocopherols, fatty acids and glycerides of fatty acids which comprises:

forming a mixture of the deodorizer sludge and a solution of urea dissolved in a solvent for urea, the molar ratio of urea to total fatty acids and glycerides of fatty acids being from about 5:1 to about 25:1 and the molar ratio of urea to solvent for urea being from about 1:1 to about 1:75, heating the mixture to form a urea complex of the fatty acids and glycerides of fatty acids, cooling the mixture to precipitate the urea complex from the mother liquor containing the tocopherols, and separating the mother liquor from the precipitate.

2. A process according to claim 1 which further comprises:

concentrating the mother liquor after separation from the precipitate, and then separating residual solids from the mother liquor.

3. A process according to claim 2 which further comprises:

extracting the mother liquor after separation from the residual solids to form an oil rich in tocopherols.

4. A process according to claim 1, 2 or 3, wherein said molar ratio of urea to total fatty acids and glycerides of fatty acids is from about 13.5:1 to about 14.5:1.

5. A process according to claim 1, 2 or 3 wherein said molar ratio of urea to solvent for urea is from about 1:1 to about 1:40.

6. A process according to claim 1, 2 or 3 wherein said heating of the mixture is at a temperature of from about 40° C. to about 78° C.

7. A process according to claim 6 wherein said solvent for urea is methanol and said heating temperature is about 64° C.

8. A process according to claim 6 wherein said solvent for urea is ethyl alcohol and said heating temperature is about 78° C.

9. A process according to claim 1, 2 or 3 wherein said heating of the mixture is conducted for a period of from about 15 minutes to about 90 minutes.

10. A process according to claim 9 wherein said heating of the mixture is conducted for about 60 minutes.

11. A process according to claim 1, 2 or 3 wherein said cooling of the mixture is to a temperature of about 0° C.–5° C.

12. A process according to claim 3 wherein said extracting of said mother liquor is performed with chloroform.

13. A process according to claim 3 wherein said extracting of said mother liquor is performed with hexane.

14. A process according to claim 3 wherein said extracting of said mother liquor is performed with methylene chloride.

* * * * *